(12) United States Patent
Hagiya et al.

(10) Patent No.: US 6,855,543 B1
(45) Date of Patent: Feb. 15, 2005

(54) PLASMID DNA CONTAINING REPORTER GENE DNA AND USE OF THE SAME

(75) Inventors: Hiroshi Hagiya, Osaka (JP); Masashi Minami, Osaka (JP); Hisao Tajima, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/446,634

(22) PCT Filed: Jun. 23, 1998

(86) PCT No.: PCT/JP98/02785

§ 371 (c)(1),
(2), (4) Date: Dec. 23, 1999

(87) PCT Pub. No.: WO99/00491

PCT Pub. Date: Jan. 7, 1999

(30) Foreign Application Priority Data

Jun. 27, 1997 (JP) .............................. 9/171440

(51) Int. Cl.[7] .............................. C12N 15/63
(52) U.S. Cl. ................... 435/320.1; 435/69.1; 536/23.1
(58) Field of Search ............................ 435/320.1, 69.1, 435/325, 69.7; 536/23.1, 23.4; 530/350; 514/44

(56) References Cited

U.S. PATENT DOCUMENTS 5,972,899 A * 10/1999 Zychlinsky et al. .......... 514/44

FOREIGN PATENT DOCUMENTS

| JP | 7-316200 | 12/1995 |
| JP | 9-504111 | 4/1997 |
| WO | WO 95/02684 | 1/1995 |
| WO | WO 95/18380 | 7/1995 |
| WO | 9640128 | 12/1996 |
| WO | WO 97/03998 | 2/1997 |

OTHER PUBLICATIONS

Oehm et al (1992, J. Biol. Chem., vol. 267, pp. 10709–10715).*
Adach et al ( Proc. Natl. Acad. Sci. USA, vol. 90, pp. 1756–1760).*
Braselmann et al (Proc Natl Acad Sci U S A. Mar. 1, 1993;90(5):1657–61).*
Itoh et al (1991, Cell, vol. 66, pp. 233–243).*
Merdan et al (Adv Drug Deliv Rev Sep. 13, 2002 vol. 54, 715, abstract only).*
Forre et al (2000, Scand J Rheuatol. vol. 29, pp. 73–84).*
Jain (Sci. Am., 1994, 271:58–65).*
Curti (Crit. Rev. in Oncology/Hematology, 1993, 14:29–39).*
Hartwell et al (Science, 1997, 278:1064–1068).*
Gura (Science, 1997, 278:1041–1042).*
Kawaguchi Y. et al, "Expression of Fas–estrogen receptor fusion protein induces cell death in pancreatic cancer cell lines" Cancer Letters, vol. 116 (1997) p. 53–59 (a copy was submitted to the USPTO by WIPO).
International Search Report.
CELL, vol. 83, No. 5, pp. 803–812 (1995).
Cancer Research, vol. 56, No. 18, pp. 4164–4170 (1996).
European Search Report.

* cited by examiner

Primary Examiner—Larry R. Helms
Assistant Examiner—Misook Yu
(74) Attorney, Agent, or Firm—Sughrue Mion, PLLC

(57) ABSTRACT

A plasmid DNA comprising a novel reporter gene DNA; a transformant transformed with the above plasmid DNA and a DNA encoding a known effector protein; a therapeutic agent for a cancer or an autoimmune disease, comprising both of the above DNAs as active ingredients; and a method for detecting a ligand of an intracellular receptor, comprising using the above transformant.

4 Claims, 4 Drawing Sheets

(A)

(B)

(A)

(B)

(A)

(B)

SEQUENCE LISTING

<160> NUMBER OF SEQ ID NOS: 24

<210> SEQ ID NO 1
<211> LENGTH: 37
<212> TYPE: DNA
<213> ORGANISM: Artificial sequence -continued

```
<220> FEATURE:
<223> OTHER INFORMATION: Primer F1

<400> SEQUENCE: 1
ccaagcttgg cgaccagcaa tacaaactgc aggaaac                              37

<210> SEQ ID NO 2
<211> LENGTH: 32
<212> TYPE: DNA
<213> ORGANISM: Artificial sequence
<220> FEATURE:
<223> OTHER INFORMATION: Primer R1

<400> SEQUENCE: 2
tcaggatcca gacattgtcc ttcattttca tt                                   32

<210> SEQ ID NO 3
<211> LENGTH: 26
<212> TYPE: DNA
<213> ORGANISM: Artificial sequence
<220> FEATURE:
<223> OTHER INFORMATION: Primer F2

<400> SEQUENCE: 3
aaccagcacc atctggtcgc gatggt                                          26

<210> SEQ ID NO 4
<211> LENGTH: 26
<212> TYPE: DNA
<213> ORGANISM: Artificial sequence
<220> FEATURE:
<223> OTHER INFORMATION: Primer R2

<400> SEQUENCE: 4
aggtgtggct gatctgaagg aactca                                          26

<210> SEQ ID NO 5
<211> LENGTH: 26
<212> TYPE: DNA
<213> ORGANISM: Artificial sequence
<220> FEATURE:
<223> OTHER INFORMATION: Primer F3

<400> SEQUENCE: 5
agaaatgacc atggttgaca cagaga                                          26

<210> SEQ ID NO 6
<211> LENGTH: 26
<212> TYPE: DNA
<213> ORGANISM: Artificial sequence
<220> FEATURE:
<223> OTHER INFORMATION: Primer R3

<400> SEQUENCE: 6
aaatgttggc agtggctcag gactct                                          26

<210> SEQ ID NO 7
<211> LENGTH: 26
<212> TYPE: DNA
<213> ORGANISM: Artificial sequence
<220> FEATURE:
<223> OTHER INFORMATION: Primer F4

<400> SEQUENCE: 7
agatcagcca tggagcagcc acagga                                          26
```

```
<210> SEQ ID NO 8
<211> LENGTH: 26
<212> TYPE: DNA
<213> ORGANISM: Artificial sequence
<220> FEATURE:
<223> OTHER INFORMATION: Primer R4

<400> SEQUENCE: 8
attggagtct gcagggaggc ctgggt                                         26

<210> SEQ ID NO 9
<211> LENGTH: 37
<212> TYPE: DNA
<213> ORGANISM: Artificial sequence
<220> FEATURE:
<223> OTHER INFORMATION: Primer F5

<400> SEQUENCE: 9
gcaagcttca ccatgaagct actgtcttct atcgaac                             37

<210> SEQ ID NO 10
<211> LENGTH: 33
<212> TYPE: DNA
<213> ORGANISM: Artificial sequence
<220> FEATURE:
<223> OTHER INFORMATION: Primer R5

<400> SEQUENCE: 10
agccatggcc ggcgatacag tcaactgtct ttg                                 33

<210> SEQ ID NO 11
<211> LENGTH: 62
<212> TYPE: DNA
<213> ORGANISM: Artificial sequence
<220> FEATURE:
<223> OTHER INFORMATION: Primer F6

<400> SEQUENCE: 11
gccatggctc ctaagaagaa gcgtaaggta ggatcccata atgccatcag gtttgggcgg    60
at                                                                   62

<210> SEQ ID NO 12
<211> LENGTH: 69
<212> TYPE: DNA
<213> ORGANISM: Artificial sequence
<220> FEATURE:
<223> OTHER INFORMATION: Primer R6

<400> SEQUENCE: 12
cctctagact agctggcata gtcgggcacg tcgtaggggt agtcgacgta caagtccttg    60
tagatctcc                                                            69

<210> SEQ ID NO 13
<211> LENGTH: 33
<212> TYPE: DNA
<213> ORGANISM: Artificial sequence
<220> FEATURE:
<223> OTHER INFORMATION: Primer F7

<400> SEQUENCE: 13
cacggatccc acaacgcgat tcgttttgga cga                                 33
```

```
<210> SEQ ID NO 14
<211> LENGTH: 33
<212> TYPE: DNA
<213> ORGANISM: Artificial sequence
<220> FEATURE:
<223> OTHER INFORMATION: Primer R7

<400> SEQUENCE: 14
atggtcgacg tacatgtccc tgtagatctc ctg                           33

<210> SEQ ID NO 15
<211> LENGTH: 33
<212> TYPE: DNA
<213> ORGANISM: Artificial sequence
<220> FEATURE:
<223> OTHER INFORMATION: Primer F8

<400> SEQUENCE: 15
cacggatccc acaacgctat ccgttttggt cgg                           33

<210> SEQ ID NO 16
<211> LENGTH: 33
<212> TYPE: DNA
<213> ORGANISM: Artificial sequence
<220> FEATURE:
<223> OTHER INFORMATION: Primer R8

<400> SEQUENCE: 16
atggtcgacg tacatgtcct tgtagatctc ctg                           33

<210> SEQ ID NO 17
<211> LENGTH: 38
<212> TYPE: DNA
<213> ORGANISM: Artificial sequence
<220> FEATURE:
<223> OTHER INFORMATION: Multicloning site DNA linker- sense strand

<400> SEQUENCE: 17
gaattcgtcg acggtaccga tatcgagctc gcggccgc                      38

<210> SEQ ID NO 18
<211> LENGTH: 85
<212> TYPE: DNA
<213> ORGANISM: Artificial sequence
<220> FEATURE:
<223> OTHER INFORMATION: GAL4 responsive element

<400> SEQUENCE: 18
tcgacggagt actgtcctcc gcgacggagt actgtcctcc gcgacggagt actgtcctcc    60
gcgacggagt actgtcctcc gagct                                         85

<210> SEQ ID NO 19
<211> LENGTH: 20
<212> TYPE: DNA
<213> ORGANISM: Artificial sequence
<220> FEATURE:
<223> OTHER INFORMATION: GAL4 responsive element

<400> SEQUENCE: 19
cgacggagta ctgtcctccg                                          20

<210> SEQ ID NO 20
<211> LENGTH: 9
<212> TYPE: PRT
<213> ORGANISM: Artificial sequence
```

```
<220> FEATURE:
<223> OTHER INFORMATION: Influenza hemagglutinin epitope

<400> SEQUENCE: 20

Tyr Pro Tyr Asp Val Pro Asp Tyr Ala
1               5

<210> SEQ ID NO 21
<211> LENGTH: 38
<212> TYPE: DNA
<213> ORGANISM: Artificial sequence
<220> FEATURE:
<223> OTHER INFORMATION: Multicloning site DNA linker- antisense strand

<400> SEQUENCE: 21
gcggccgcga gctcgatatc ggtaccgtcg acgaattc                              38

<210> SEQ ID NO 22
<211> LENGTH: 335
<212> TYPE: PRT
<213> ORGANISM: Homo sapiens

<400> SEQUENCE: 22

Met Leu Gly Ile Trp Thr Leu Leu Pro Leu Val Leu Thr Ser Val Ala
    -15                 -10                 -5                  -1

Arg Leu Ser Ser Lys Ser Val Asn Ala Gln Val Thr Asp Ile Asn Ser
1               5                   10                  15

Lys Gly Leu Glu Leu Arg Lys Thr Val Thr Thr Val Glu Thr Gln Asn
            20                  25                  30

Leu Glu Gly Leu His His Asp Gly Gln Phe Cys His Lys Pro Cys Pro
        35                  40                  45

Pro Gly Glu Arg Lys Ala Arg Asp Cys Thr Val Asn Gly Asp Glu Pro
    50                  55                  60

Asp Cys Val Pro Cys Gln Glu Gly Lys Glu Tyr Thr Asp Lys Ala His
65                  70                  75                  80

Phe Ser Ser Lys Cys Arg Arg Cys Arg Leu Cys Asp Glu Gly His Gly
                85                  90                  95

Leu Glu Val Glu Ile Asn Cys Thr Arg Thr Gln Asn Thr Lys Cys Arg
            100                 105                 110

Cys Lys Pro Asn Phe Phe Cys Asn Ser Thr Val Cys Glu His Cys Asp
        115                 120                 125

Pro Cys Thr Lys Cys Glu His Gly Ile Ile Lys Glu Cys Thr Leu Thr
    130                 135                 140

Ser Asn Thr Lys Cys Lys Glu Glu Gly Ser Arg Ser Asn Leu Gly Trp
145                 150                 155                 160

Leu Cys Leu Leu Leu Leu Pro Ile Pro Leu Ile Val Trp Val Lys Arg
                165                 170                 175

Lys Glu Val Gln Lys Thr Cys Arg Lys His Arg Lys Glu Asn Gln Gly
            180                 185                 190

Ser His Glu Ser Pro Thr Leu Asn Pro Glu Thr Val Ala Ile Asn Leu
        195                 200                 205

Ser Asp Val Asp Leu Ser Lys Tyr Ile Thr Thr Ile Ala Gly Val Met
    210                 215                 220

Thr Leu Ser Gln Val Lys Gly Phe Val Arg Lys Asn Gly Val Asn Glu
225                 230                 235                 240

Ala Lys Ile Asp Glu Ile Lys Asn Asp Asn Val Gln Asp Thr Ala Glu
                245                 250                 255
```

-continued

```
Gln Lys Val Gln Leu Leu Arg Asn Trp His Gln Leu His Gly Lys Lys
            260                 265                 270
Glu Ala Tyr Asp Thr Leu Ile Lys Asp Leu Lys Lys Ala Asn Leu Cys
        275                 280                 285
Thr Leu Ala Glu Lys Ile Gln Thr Ile Ile Leu Lys Asp Ile Thr Ser
    290                 295                 300
Asp Ser Glu Asn Ser Asn Phe Arg Asn Glu Ile Gln Ser Leu Val
305                 310                 315

<210> SEQ ID NO 23
<211> LENGTH: 327
<212> TYPE: PRT
<213> ORGANISM: Mus musculus

<400> SEQUENCE: 23

Met Leu Trp Ile Trp Ala Val Leu Pro Leu Val Leu Ala Gly Ser Gln
        -20                 -15                 -10
Leu Arg Val His Thr Gln Gly Thr Asn Ser Ile Ser Glu Ser Leu Lys
-5               -1   1               5                  10
Leu Arg Arg Arg Val His Glu Thr Asp Lys Asn Cys Ser Glu Gly Leu
             15                  20                  25
Tyr Gln Gly Gly Pro Phe Cys Cys Gln Pro Cys Gln Pro Gly Lys Lys
         30                  35                  40
Lys Val Glu Asp Cys Lys Met Asn Gly Gly Thr Pro Thr Cys Ala Pro
     45                  50                  55
Cys Thr Glu Gly Lys Glu Tyr Met Asp Lys Asn His Tyr Ala Asp Lys
60                  65                  70                  75
Cys Arg Arg Cys Thr Leu Cys Asp Glu Glu His Gly Leu Glu Val Glu
             80                  85                  90
Thr Asn Cys Thr Leu Thr Gln Asn Thr Lys Cys Lys Cys Lys Pro Asp
             95                 100                 105
Phe Tyr Cys Asp Ser Pro Gly Cys Glu His Cys Val Arg Cys Ala Ser
         110                 115                 120
Cys Glu His Gly Thr Leu Glu Pro Cys Thr Ala Thr Ser Asn Thr Asn
     125                 130                 135
Cys Arg Lys Gln Ser Pro Arg Asn Arg Leu Trp Leu Leu Thr Ile Leu
140                 145                 150                 155
Val Leu Leu Ile Pro Leu Val Phe Ile Tyr Arg Lys Tyr Arg Lys Arg
                 160                 165                 170
Lys Cys Trp Lys Arg Arg Gln Asp Asp Pro Glu Ser Arg Thr Ser Ser
             175                 180                 185
Arg Glu Thr Ile Pro Met Asn Ala Ser Asn Leu Ser Leu Ser Lys Tyr
         190                 195                 200
Ile Pro Arg Ile Ala Glu Asp Met Thr Ile Gln Glu Ala Lys Lys Phe
     205                 210                 215
Ala Arg Glu Asn Asn Ile Lys Glu Gly Lys Ile Asp Glu Ile Met His
220                 225                 230                 235
Asp Ser Ile Gln Asp Thr Ala Glu Gln Lys Val Gln Leu Leu Leu Cys
             240                 245                 250
Trp Tyr Gln Ser His Gly Lys Ser Asp Ala Tyr Gln Asp Leu Ile Lys
         255                 260                 265
Gly Leu Lys Lys Ala Glu Cys Arg Arg Thr Leu Asp Lys Phe Gln Asp
     270                 275                 280
```

```
Met Val Gln Lys Asp Leu Gly Lys Ser Thr Pro Asp Thr Gly Asn Glu
    285                 290                 295

Asn Glu Gly Gln Cys Leu Glu
300                 305

<210> SEQ ID NO 24
<211> LENGTH: 9
<212> TYPE: PRT
<213> ORGANISM: Artificial sequence
<220> FEATURE:
<223> OTHER INFORMATION: T antigen-originated nuclear transport signal

<400> SEQUENCE: 24

Ala Pro Lys Lys Lys Arg Lys Val Gly
1               5
```

US 6,855,543 B1

PLASMID DNA CONTAINING REPORTER GENE DNA AND USE OF THE SAME

TECHNICAL FIELD

The invention relates to (i) a plasmid DNA comprising a novel reporter gene DNA, (ii) a transformant transformed with the above plasmid DNA and a DNA encoding a known effector protein, (iii) a therapeutic agent for a cancer or an autoimmune disease, comprising both of the above DNAs as active ingredients, and (iv) a method for detecting a ligand of an intracellular receptor, comprising using the above transformant.

More particularly, the invention relates to (i) a plasmid DNA comprising a novel reporter gene, namely a minimum essential promoter and a DNA encoding an amino acid sequence comprising a transmembrane region and a functional region of an Fas antigen for detecting a gene expression effect, in a region downstream of an enhancer element in which a responsive element of Gal4 protein which is a yeast basal transcription factor (hereinafter referred to as "UAS") is repeated several times, (ii) a transformant transformed with both of the above plasmid DNA and a DNA encoding a fusion protein in which an amino acid sequence comprising a ligand binding region of an intracellular receptor is linked to the C-terminal of an amino acid sequence comprising the DNA binding region of a known effector protein, namely Gal4 protein, (iii) a therapeutic agent for a cancer or an autoimmune disease, comprising both of the above DNAs as active ingredients and (iv) a method for detecting an intracellular receptor ligand, comprising using the above transformant.

BACKGROUND ART

Recently, receptors of humoral factors having important physiological activities, typified by cytokine and hormones, have been revealed by gene manipulation, and a large number of receptors have been isolated and identified. The examples include receptors of lipophilic hormones generally referred to as intracellular receptors. As a result of the analysis of amino acid sequences of various intracellular receptors, it was revealed that they are ligand-dependent transcription factors having a common basic structure and forming one of gene family. That is, they belong to a family including a steroid receptor, such as glucocorticoid receptor, progesterone receptor, mineral corticoid receptor, androgen receptor, estrogen receptor and the like; a retinoid receptors, such as retinoid X receptor, retinoic acid receptor and the like; a peroxisome proliferator-activated receptor; a vitamin $D_3$ receptor; and a thyroid hormone receptor. Since it has been revealed that functional regions, such as a ligand binding domain and a domain which recognizes a target DNA sequence and the like, are distinctively separated in these receptors (see Science, 240, 889 (1988)), they have been isolated based on the homology, though there are certain receptors whose ligands are still unknown.

Recently, a nuclear receptor, peroxisome proliferator-activated receptor (hereinafter referred to as a "PPAR receptor"), is drawing attention in the field of studies on transcription factors related to the expression and induction of fat cell differentiation marker genes. Regarding the PPAR receptor, cDNA has been cloned from various animal species, and a plurality of isoform genes have been found including α, δ and γ types in mammals. In addition, R1 is known that the γ0 type is expressed in fat tissues, immunocytes, adrenal gland, spleen and small intestine, and the a type in liver and retinas, but the δ type has no tissue specificity and is expressed ubiquitously.

On the other hand, Fas antigen is a membrane protein whose participation in programmed cell death, namely apoptosis has been clearly shown. Yonehara et al. have prepared monoclonal antibodies for human cell surface antigens and obtained an anti-Fas antibody showing lethal activity upon various human cells (see J. Exp. Med., 169, 1747 (1989)), cDNA of a cell surface molecule recognizable by the anti-Fas antibody has been isolated, and structure of the human Fas antigen has been determined (SEQ ID NO:22) (see Cell, 66, 233 (1991)). This Fas antigen is composed of 335 amino acid residues, and 16 amino acid residues in the N-terminus is assumed to be its signal peptide. A transmembrane region composed of 17 hydrophobic amino acid residues is present in a central position of the molecule, and it is considered that 157 amino acid residues in the N-terminus exist as its extracellular region and the C-terminal side sequence of 145 amino acid residues is its cytoplasmic region.

Since the structure of the Fas antigen is resemble in the structure of a receptor for tumor necrosis factor (TNF), it is assumed that the apoptosis of the Fas antigen occurs by a mechanism similar to the action of TNF. Functional regions of the Fas antigen have also been revealed gradually, and it has been found that the region essential for the signal transduction of apoptosis (functional region) is an amino acid sequence of the 175 h to 304' positions (see J. Biol. Chem, 268, 10932 (1993)). In addition, the amino acid sequence of mouse Fas antigen has also been revealed (SEQ ID NO:23) (see J. Immunology, 148, 1274 (1992)), and it has a homology of 49.3% to the human Fas antigen as a whole. It is considered also that its functional region is an amino acid sequence of the $166^{th}$ to $291^{st}$ positions corresponding to the region of the human Fas antigen.

Receptors have a ligand binding region and a signalling transduction region. When a ligand is linked to the ligand binding region, the stereostructure of the signal transfer region is changed and a signal is transferred to other protein or DNA.

Recently, many studies have been conducted positively on the intercellular signal transduction by a fusion protein in which the ligand binding region of a receptor is linked to the signalling region of a different protein.

For example, it has been revealed that, in the case of cells transformed with a gene encoding a fusion protein of the ligand binding region of an estrogen receptor which is one of steroid receptors family, and the fanctional region of human cancer gene c-Myc, the cells are cancerated to abnormally proliferate by the stimulation of the ligand, estrogen (see Nature, 340, 66 (1989)).

Similar studies have been carried out on fusion proteins of the ligand binding region of each of the receptors for glucocorticoid, mineral corticoid and estrogen with the functional region of each of the proteins of E1A (adenovirus), c-Fos, v-Myb, C/EBP, v-Re1, GATA-1, 2 and 3, GAL4-VP16, Rev (HIV) and c-Ab1 (see Cell, 54, 1073 (1988), Proc. Natl. Acad. Sci. USA, 88, 5114 (1991), EMBO J., 10, 3713 (1991), Science, 251, 288 (1991), EMBO J., 11, 4641 (1992), Genes Dev. (in press), Proc. Nat. Acad. Sci. USA, 90, 1657 (1993), ibid., 87, 7787 (1990) and EMBO J., 12, 2809 (1993)), confirming that respective signals are transferred by the binding of ligands to their corresponding nuclear receptors.

Kakizuka et al. have reported a method in which the Fas antigen is used as a signal transduction protein for applying the above fusion protein to the treatment of a cancer (see JP-A-7-316200). In this method, an amino acid sequence of the 136th to 305th positions including not only the functional region but also the transmembrane region is fused with the ligand binding region of the intracellular receptor. As a result, a ligand capable of interacting with the amino acid sequence of the nuclear receptor ligand binding region can be detected effectively.

On the other hand, R. M. Evans et al. have reported a reporter assay method in which a reporter using an enzyme capable of converting a substrate into a chemiluminescent or visible dye product or introducing a substituent (e.g., luciferase, β-galactosidase, secretory alkaline phosphatase, or chloramphenicol acetyltransferase) in a region downstream of the Gal4 responsive element and a protein prepared by fusing the Gal4 DNA binding domain and the PPAR receptor ligand binding region are introduced into cells (see PCT International Application International Publication No. 9640128). Another assay method has also been reported in which, either by expressing an exogenous PPAR receptor protein or along with an endogenous PPAR receptor protein, the above reporter, with the proviso that in this case, the reporter is a reporter using the above enzyme in a region downstream of PPAR receptor responsive element (hereinafter referred to as "PPRE") are introduced (*Cell,* 0, 803 (1995)). These assay systems are detection systems which can evaluate the function of intracellular receptors as transcription factors.

However, since these methods require a certain period of time for the activity detection, it is difficult to carry out high speed screening of the effect of ligands and compounds to be tested. In addition, since the introduction of DNA into cells is transient, it causes a problem in that the results cannot easily be compared due to insufficient stability among tests.

DISCLOSURE OF THE INVENTION

For carrying out high speed screening of compounds which bind to ligands of intracellular receptors as an object, the inventors of the invention have conducted intensive studies and found, as a result of the efforts, that the object can be attained using a reporter assay in which an Fas protein is expressed.

That is, an expression vector comprising a reporter using a functional region of an Fas structural protein and a DNA encoding a protein prepared by fusing a DNA binding region of Gal4 and a nuclear receptor (particularly PPAR receptor) ligand binding region was stably introduced into mouse fibroblast L929 cells. These cells were able to grow under such conditions that ligands or compounds did not bind to the amino acid sequence of the nuclear receptor ligand binding region, but cell death occurred due to expression induction of an Fas protein when the ligands or compounds bound to the sequence. Thereafter, we have succeeded in carrying out high speed screening of a compound which interacts with the ligand binding region of an intracellular receptor and can functionally increase or decrease the activity of transcription factor by separating the thus cell death-caused cells from intact cells, staining the intact cells with a dye, and measuring the absorbance of the stained cells.

The high throughput screening method with the high speed of the invention is a novel method which has been unknown completely.

In the method of the invention, the measurement is carried out by generating cell death through expression of an Fas protein using functional region as a reporter of an Fas protein, so that it is completely different from the method of R. M. Evans et al. using an enzyme which generates chemiluminescence (particularly luciferase) or forms a visible dye (particularly β-galactosidase) as the reporter and measuring the amount of expressed the enzyme (enzyme activity).

In comparing by the standard test methods, the method of R. M. Evans et al. requires an experimental period for 4 days at the shortest in which DNA is introduced into cells and serum stimulation is carried out on the first day, re-inoculation is optionally carried out, a compound to be tested is added after 46 to 48 hours (on the third day), and luciferase activity is measured 24 hours thereafter (on the final day). Also, since the introduction of DNA into cells is transient, it causes a problem in terms of stability and comparison between tests.

r. An expression vector comprising a DNA encoding another enzyme may be co-introduced in order to compare each measurements, but the handling becomes complex. In addition, since the measured value greatly varies, the method using luciferase requires a large number of cases (generally requires an n number of 3 to 4). Alternatively, it is necessary to standardize the method with a simultaneously introduced internal standard gene (e.g., β-galactosidase gene etc.) as described above.

On the other hand, the invention is a method of two-day schedule at the shortest, in which, when cells are prepared in advance, a compound to be tested is added on the first day, and the cells can be measured by a dye staining on the latter half of the next day (after 36 hours). Also, since L929 cells (the same clone) are used, comparison between tests can be made easily. In addition, since the variation of values is small when measured by the method of the invention in which stably introduced cells are used, it does not require a large number of cases (generally, sufficient judgment can be made by an n number of 1 to 2).

Thus, according to the method of the invention, it is possible to carry out high speed evaluation of ligands and compounds which can change functions of intracellular receptors, and the handling per se is simple and easy. Also, since variation of measured values is small, data between tests can be easy to compare and are very stable. These advantages exert full abilities particularly in the high speed evaluation of multiple samples. In addition, since an absorbance measuring apparatus is attached to any generally and practically used automatic analyzers (robotic machine) as a standard measure, the method can be regarded as a robot-corresponding compound evaluation system. This is a fact which cannot be expected from the previous art but confirmed for the first time by experiments carried out by the present inventors. In addition, since the method of the invention require no enzyme substrate, sharp reduction of cost can be made.

DETAILED DESCRIPTION OF THE INVENTION

Figure 1:
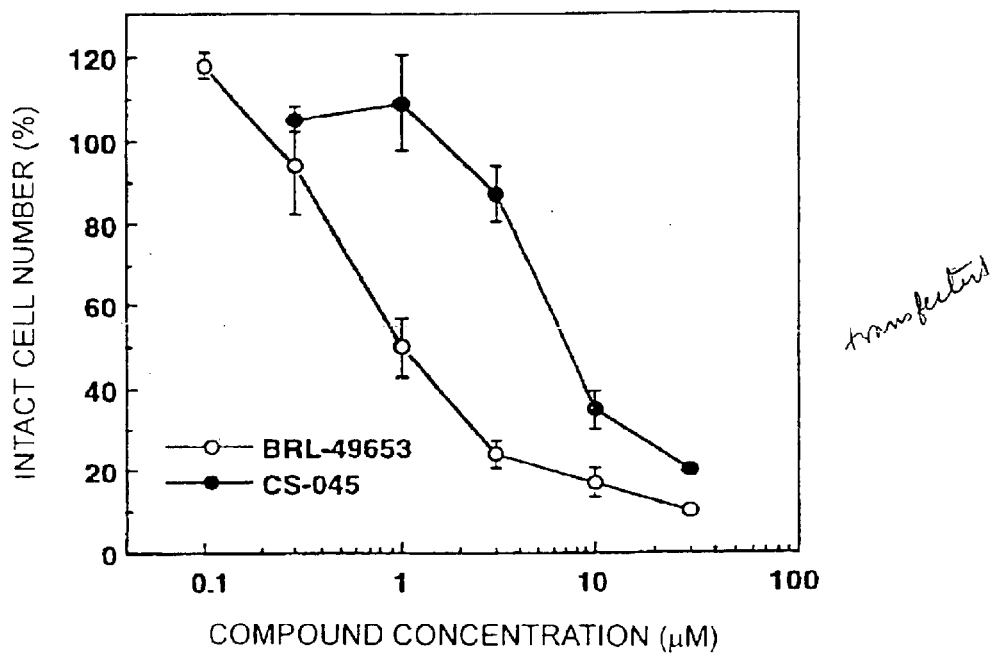
FIG. 1 is a graph showing dose-dependent changes in the number of intact cells after treatment of each compound by carrying out a cell death assay using PPAR γ ligand-responsive L929 cells. In the drawing, (A) shows a case of PPAR γ ligand-responsive cells, and (B) shows a case of normal L929 cells.
Figure 1:
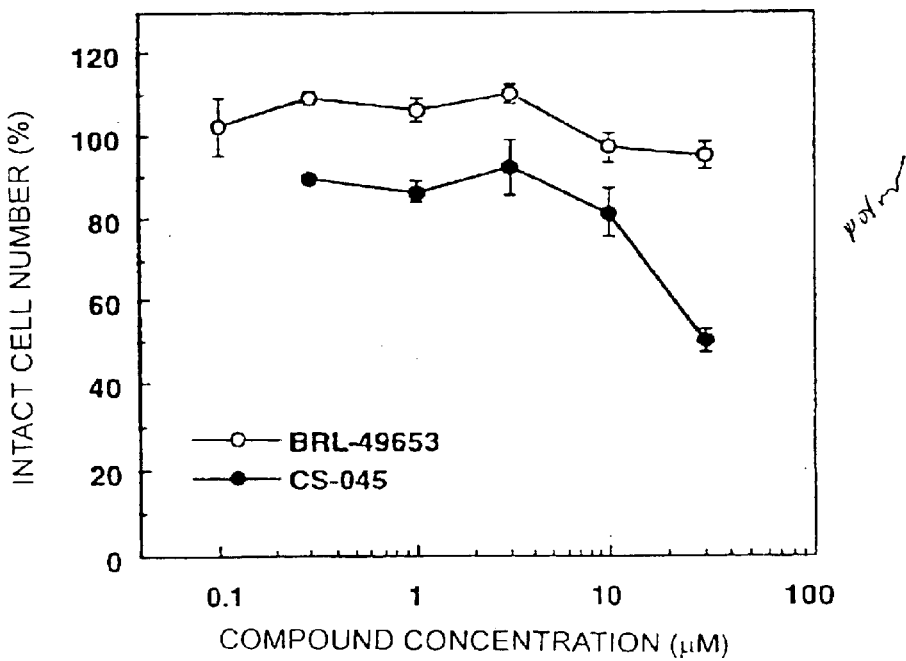

The invention relates to
(i) a novel plasmid DNA comprising a reporter gene DNA,
(ii) a transformant transformed with the above plasmid DNA and a DNA encoding a known effector protein,
(iii) a therapeutic agent for a cancer or autoimmune disease, comprising both of the above DNAs as active ingredients, and
(iv) a method for detecting a ligand of an intracellular receptor, comprising using the transformant.

The Fas antigen and intracellular receptor for use in the invention are those which are originated from mammals, such as humans, monkeys, dogs, cats, mice, rats and guinea pigs. The Fas antigen and intracellular receptor are preferably originated from the same species, but those from the different species can also be used. It has been confirmed by the invention that the transfer of signals can be effected when those which are originated from different species are used. For example, a combination of human Fas antigen with a human intracellular receptor, a combination of mouse Fas antigen with a human intracellular receptor, a combination of human Fas antigen with a rat intracellular receptor, a combination of mouse Fas antigen with a rat intracellular receptor, a combination of human Fas antigen with a mouse intracellular receptor or a combination of mouse Fas antigen with a mouse intracellular receptor can be used suitably.

As the amino acid sequence comprising the transmembrane region and the function expressing region of an Fas antigen and the amino acid sequence comprising the ligand binding region of an intracellular receptor for use in the invention, the portion corresponding to each region may be used alone, or the portion corresponding to each region may further contain a flanking region (a region which does not take part in the functional region; several tens, preferably 60 or less, of residues as an amino acid sequence) on its both termini (N-terminal and/or C-terminal). If desired, an amino acid sequence comprising a signal peptide region may be linked to the N-terminal of the transmembrane region of the Fas antigen. The amino acid sequence corresponding to each region may be not only a natural amino acid sequence but also its derivative in which at least one amino acid is deleted, substituted, added and/or inserted in a such extent that the original apoptosis function of the Fas antigen or the ligand binding function of the intracellular receptor is not spoiled.

Among the Fas antigens for use in the invention, the amino acid sequence comprising the transmembrane region and the function expressing region of the human Fas antigen is a sequence of the 145th Ser to the 319th Val, and, in the case of the mouse Fas antigen, a sequence of the 136th Ser to the 305th Leu is preferably used. Also, as the amino acid sequence comprising a signal peptide region, a sequence of the −16th to 23rd positions of human Fas antigen or a sequence of the −21st to 14th positions of mouse Fas antigen is preferably used.

Examples of the intracellular receptor in the effector protein for use in the invention include a steroid receptor, such as a glucocorticoid receptor, a progesterone receptor, a mineral corticoid receptor, an androgen receptor, an estrogen receptor and the like; a retinoid receptor, such as retinoid X receptor, retinoic acid receptor and the like; a peroxisome proliferator-activated receptor; a vitamin D, receptor; and a thyroid hormone receptor. Among these, human or rat estrogen receptor; human or mouse retinoid X receptor α, retinoid X receptor β or retinoid X receptor γ; human or mouse retinoic acid receptor α, retinoic acid receptor β or retinoic acid receptor γ; human or mouse PPAR α receptor; human or mouse PPAR δ receptor; and human or mouse PPAR γ receptor are preferably used.

The ligand binding region of each receptor is already known (see Science, 240, 889 (1988); Mol. Endocrinology, 6, 1634 (1992); Biochem. Biophys. Res. Commun., 224, 431 (1996); J. Steroid Biochem. Molec. Biol., 51, 157 (1994); and Proc. Natl. Acad. Sci. USA, 91, 7355 (1994)), such as 528th to 777th positions in the human glucocorticoid receptor, the 680th to 934th positions in the human progesterone receptor, the 734th to 984th positions in the human mineral corticoid receptor, the 676th to 919th positions in the human androgen receptor, the 311th to 551st positions in the human estrogen receptor, the 307th to 557th positions in the rat estrogen receptor, the 225th to 462nd positions in the human retinoid X a receptor a, the 297th to 526th positions in the human retinoid X receptor β the 230th to 467th positions in the mouse retinoid X receptor α, the 171st to 410th positions in the mouse retinoid X receptor β, the 229th to 463rd positions in the mouse retinoid X receptor γ, the 198th to 462nd positions in the human retinoic acid receptor α, the 191st to 448th positions in the human retinoic acid receptor β, the 200th to 454th positions in the human retinoic acid receptor γ, the 198th to 462nd positions in the mouse retinoic acid receptor at, the 190th to 448th positions in the mouse retinoic acid receptor β, the 200th to 458th positions in the mouse retinoic acid receptor γ, the 192nd to 427th positions in the human vitamin $D_3$ receptor, the 183rd to 410th positions in the human thyroid hormone receptor α, the 232nd to 456th positions in the human thyroid hormone receptor β, the 280th to 478th positions in the human PPAR γ (human PPAR γ1 subtype) receptor, the 278th to 475th positions in the mouse PPAR γ (mouse PPAR γ1 subtype) receptor, the 273rd to 468th positions in human PPAR a receptor, the 273rd to 468th positions in the mouse PPAR β receptor, the 273rd to 468th positions in rat PPAR a receptor, the 246th to 441st positions in the human PPAR γ receptor, and the 245th to 440th positions in the mouse PPAR δ receptor.

Preferred examples include a sequence of the 311th position to the 551st position of the human estrogen receptor, the 307th to 557th positions of the rat estrogen receptor, the 225th to 462nd positions of the human retinoid X receptor ox, the 297th to 526th positions of the human retinoid X receptor β, the 230th to 467th positions of the mouse retinoid X receptor α, the 171st to 410th positions of the mouse retinoid X receptor β, the 229th to 463rd positions of the mouse retinoid X receptor γ, the 198th to 462nd positions of the human retinoic acid receptor α, the 191st to 448th positions of the human retinoic acid receptor β, the 200th to 454th positions of the human retinoic acid receptor γ, the 198th to 462nd positions of the mouse retinoic acid receptor α, the 190th to 448th positions of the mouse retinoic acid receptor β, the 200th to 458th positions of the mouse retinoic acid receptor γ, the 176th to 478th positions of the human PPAR γ (human PPAR γ1 subtype) receptor, the 174th to 475th positions of the mouse PPAR γ (mouse PPAR γ1 subtype) receptor, the 167th to 468th positions of the human PPAR a receptor, the 167th to 468th positions of the mouse PPAR α receptor, the 167th to 468th positions of the rat PPAR a receptor, the 139th to 441st positions of the human PPAR γ receptor, and the 138th to 440th positions of the mouse PPAR γ receptor.

More preferred examples include a sequence of the 281st to 595th positions of the human estrogen receptor, the 286th to 600th positions of the rat estrogen receptor, the 176th to 462nd positions of the human retinoic acid receptor α, the 177th to 458th positions of the mouse retinoic acid receptor α, the 166th to the 478th positions of the human PPAR γ (human PPAR γ1 subtype) receptor (corresponding to a sequence of the 194th to 506th positions of the human PPAR γ2 subtype), the 164th to 475th positions of the mouse PPAR γ (mouse PPAR γ1 subtype) receptor (corresponds to a sequence of the 194th to 505th positions of the mouse PPAR y2 subtype), the 157th to 468th positions of the human PPAR a receptor, the 157th to 468th positions of the mouse PPAR a receptor, the 157th to 468th positions of the rat PPAR α receptor, the 129th to 441st positions of the human PPAR & receptor, and the 128th to 440th positions of the mouse PPAR 3 receptor.

Examples of more preferred effector protein for use in the invention include:
(i) an effector protein in which an amino acid sequence of the 176th serine (Ser) to the 478th tyrosine (Tyr) of the human PPAR γ1 receptor is linked to the C-terminal of an amino acid sequence of the 1st to 147th positions of the DNA binding region of Gal4 protein,
(ii) an effector protein in which an amino acid sequence of the 174th serine (Ser) to the 475th tyrosine (Tyr) of the mouse PPAR γ1 receptor is linked to the C-terminal of an amino acid sequence of the 1st to 147th positions of the DNA binding region of Gal4 protein,
(iii) an effector protein in which an amino acid sequence of the 204th serine (Ser) to the 506th tyrosine (Tyr) of the human PPAR γ2 receptor is linked to the C-terminal of an amino acid sequence of the 1st to 147th positions of the DNA binding region of Gal4 protein,
   (iv) an effector protein in which an amino acid sequence of the 204th serine (Ser) to the 505th tyrosine (Tyr) of the mouse PPAR γ2 receptor is linked to the C-terminal of an amino acid sequence of the 1st to 147th positions of the DNA binding region of Gal4 protein,
   (v) an effector protein in which an amino acid sequence of the 167th serine (Ser) to the 468th tyrosine (Tyr) of the human PPAR α receptor is linked to the C-terminal of an amino acid sequence of the 1st to 147th positions of the DNA binding region of Gal4 protein,
   (vi) an effector protein in which an amino acid sequence of the 167th serine (Ser) to the 468th tyrosine (Tyr) of the mouse PPAR at receptor is linked to the C-terminal of an amino acid sequence of the 1st to 147th positions of the DNA binding region of Gal4 protein,
(vii) an effector protein in which an amino acid sequence of the 139th serine (Ser) to the 441st tyrosine (Tyr) of the human PPAR δ receptor is linked to the C-terminal of an amino acid sequence of the 1st to 147th positions of the DNA binding region of Gal4 protein, and
(viii) an effector protein in which an amino acid sequence of the 138th serine (Ser) to the 440th tyrosine (Tyr) of the mouse PPAR γ receptor is linked to the C-terminal of an amino acid sequence of the 1st to 147th positions of the DNA binding region of Gat4 protein.

Regarding the UAS which is a Gal4 protein responsive element contained as a repeating structure in the reporter plasmid of the invention, an already known sequence was used (see (*Cell,* 83, 803 (1995) and *Cell,* 83, 813 (1995))). That is, a sequence in which a sequence of 5'-CGACGGAGTACTGTCCTCCG-3' (SEQ ID NO: 19) is repeated several times, specifically at least three 3 times, preferably 4 times, more preferably 5 times.

Examples of the promoter of the invention include SV40, HSV LTR, a metallothionein promoter, and a thymidine kinase (TK) promoter. A TK promoter is preferred. More specifically, it is preferred to use a sequence of the −727th to 56th positions of the mRNA of the TK promoter, when its transcription initiation point is regarded as the 1st position, as used in plasmid pTKβ (Clontech Laboratories, Cat. No. 6179-1) (corresponding to a sequence of the 165th to 945th positions in the pTKβ map). A sequence of the −105th to 51st positions of the mRNA of the TK promoter is more preferred.

DNAs encoding the reporter plasmid of the invention are also included in the invention. As well known, one amino acid is encoded by 1 to 6 codons U (e.g., 1 codon for methionine (Met) and 6 codons for leucine (Leu)). Accordingly, the nucleotide sequence of a DNA can be changed without changing its corresponding amino acid sequence.

Among DNAs encoding the reporter plasmid of the invention, a group of nucleotide sequences of all DNA sequences which result in the same Fas protein polypeptide are included in the invention. Productivity of the fusion protein may sometimes be improved by changing the nucleotide sequence.

The DNA encoding the reporter plasmid of the invention can be prepared in accordance with the following method.

That is, this method is carried out by
(i) amplifying DNAs encoding amino acid sequences comprising necessary regions of the amino acid sequences of an Fas antigen and an at intracellular receptor by the polymerase chain reaction (PCR), and
(ii) inserting the PCR product obtained from the Fas antigen, and subsequently the PCR product obtained from the intracellular receptor, into an appropriate vector.

In detail, the step (i) is a step in which necessary parts for fusion are amplified by PCR. In the case of the Fas antigen, a nucleotide sequence encoding an amino acid sequence comprising the transmembrane region and the function expressing region is chemically synthesized and used as a primer. Also, in the case of the intracellular receptor, a nucleotide sequence encoding an amino acid sequence comprising the ligand binding region is chemically synthesized and used as a primer.

A specific restriction enzyme site is arranged on the 5'-end of each of the thus obtained primers. Regarding the template for PCR, mRNA isolated and purified from cells or a cell line of a corresponding mammal, such as human, mouse or the like, can be used. The PCR is carried out by a known method. Since automatic PCR apparatuses have come into wide use recently, the apparatuses are suitably used.

In the step (ii), DNAs corresponding to the DNA binding region of Gal4 and the nuclear receptor ligand binding region are fused in an expression vector. As the plasmid vector for use in this step, a large number of vectors capable of functioning in *Escherichia coli* (e.g., pBR322) or *Bacillus subtilis* (e.g., pUB110) are known, and any of them can be used suitably. Also, it is possible to insert these fragments directly into an expression vector.

When expressed in mammal cells, the expression vector is prepared by inserting the PCR product of the Gal4 DNA binding region and then that of the intracellular receptor into a region downstream of an appropriate promoter (e.g., SV40 promoter, LTR promoter or metallothionein promoter) in an appropriate vector (e.g., a retrovirus vector, a papilloma virus vector, a vaccinia virus vector or an SV40 vector). Preferably, pCMX (described in Cell, 66, 663 (1991)) or pSV (described in Anal. Biochem., 188, 245 (1990)) is used.

Subsequently, in the step (iii), a reporter plasmid is produced. The plasmid vector for use in this step may be any one of those which function in E. coli or B. subtilis as described above. It can also be inserted directly into the expression vector. A plasmid comprising a DNA in which a repeating structure of Gal4 responsive element, a herpes simplex virus thymidine kinase promoter and a DNA encoding an Fas structural protein are located in a tandem from the 5' region upstream can have the purpose depending on whether its origin is a vector which can function in E. coli or mammal cells. As described above, it may further contain an ori region, a promoter controlling factor and at least one selective a marker gene. When mammal cells are used, test cells which die in an Fas protein expression-dependent manner can be obtained by transforming appropriate mammal cells using the above plasmid-capable of functioning in mammal cells and culturing the resulting transformant in an appropriate medium.

When the expression is carried out in mammal cells, a PCR product of a nucleotide sequence encoding the signal peptide region of an Fas antigen can be optionally inserted into a site immediately downstream of the promoter.

Examples of the replication or expression vector comprising the DNA of the invention include a plasmid, a virus and a phage vector comprising an on region, and optionally a promoter for the expression of the above DNA and a all controlling factor of the promoter or the like. The vector may further contain at least one selective marker gene (e.g., neomycin resistant gene, blasticidin S resistant gene).

Furthermore, as the protein expression system of the invention, the objective fusion protein can be produced by transforming appropriate mammal cells (e.g., monkey COS-7 cells, Chinese hamster CHO cells, mouse L cells, mouse fibroblasts, human cancer cells and the like) with the above expression vector which functions in mammal cells, and culturing the resulting transformant in an appropriate medium. The thus obtained polypeptide can be isolated and purified by generally used biochemical means.

The host cells transformed with a replication or expression vector comprising the DNA of the invention are included in the invention.

INDUSTRIAL APPLICABILITY

The thus obtained plasmid DNA of the invention can be used as a therapeutic agent for a cancers and an autoimmune disease. That is, an expression vector comprising the plasmid DNA of the invention is topically administered to the focal part of a cancer or autoimmune disease by a targeting method (e.g., by its inclusion in liposomes). This vector penetrates into cancer cells of the focal part and reaches genes. Thereafter, when a ligand corresponding to the intracellular receptor which constitutes a part of the effector protein of the invention (for example, 9-cis-retinoic acid when a retinoid X receptor is used as the receptor, or vitamin A when a retinoic acid receptor is used) is administered, the effector is activated and the Fas protein is expressed. The signal of apoptosis is transduced by the Fas protein produced in the cancer cells, thereby the cells become extinct.

Furthermore, the plasmid DNA of the invention can be used broadly as a screening method of an agonist or an antagonist for an intracellular receptor. That is, a sample to be tested is added to cells into which an expression vector comprising the DNA encoding the effector protein (an expression vector DNA comprising a DNA encoding the ligand binding region of various nuclear receptors in a region downstream of the Gal4 DNA binding region) and the reporter DNA for use in the present invention has been inserted. Death of the cells indicates that the sample to be tested has agonist activity, and survival of the cells in the presence of an agonist reveals that the sample has antagonist activity.

According to the screening method of the invention, high speed evaluation of ligands and compounds capable of changing functions of intracellular receptors can be conducted. Since the effects (results) are observed as cell death, the judgment is easy and the handling per se is also simple and easy. In addition, when a DNA encoding the ligand binding region of various nuclear receptors is arranged in a region downstream of the Gal4 DNA binding region as an effector protein, it becomes a method generally used which can screen compounds that act upon nuclear receptors including orphan receptors whose ligands are unknown. As a matter of course, it is possible to search for physiological ligands of orphan nuclear receptors. Specifically, it can be applied to the identification of ligands or their purification from fractions having ligand activities by adding a physiological ligand candidate to be expected or a partially fractionated sample of serum to the above cells and observing the presence or absence of cell death.

Also, since variation of values measured by the method of the invention is small, data between tests can be easy to compare and are very stable. These advantages exert full abilities particularly in the high speed evaluation of multiple samples. In addition, since an absorbance measuring apparatus is attached to any generally and practically used automatic analyzers (robotic machine) as a standard measure, the method can be regarded as a robot-corresponding compound evaluation system. Moreover, since the screening method of the invention does not require enzyme substrate, sharp reduction of cost can be made.

BEST MODE FOR CARRYING OUT THE INVENTION

The invention is described further in detail and specifically by the following examples, though the invention is not restricted thereto as a matter of course.

EXAMPLE 1

Preparation of PCR Product of Mouse Fas Antigen

The following primers were prepared based on the structure of the mouse Fas antigen in accordance with the method reported by Fukunaga et al. (see J. Immunology, 148, 1274 (1992)) or Kakizuka et al. (see JP-A-7-316200).

F1: A sense primer, 5'-CCAAGCTTGGCGACCAGCAATACAAACT GCAGGAAAC-3' (SEQ ID NO:1), corresponding to the structure of an amino acid sequence of the 131st to 143rd positions, namely Pro Cys Thr Ala Thr Ser Asn Thr Asn Cys Arg Lys Gin, in which a restriction enzyme HindIII site was introduced into a part of the 5' side, was synthesized.

R1: An antisense primer, 5'-TCAGGATCCAGACATTGTCCTTCATTT TCATT-3' (SEQ ID NO:2), corresponding to an amino acid sequence of the 298th a., to 306th positions (C-terminal), namely Asn Glu Asn Gin Gly Gin Cys Leu Glu, and a portion of the 3' non-translation region, in which a BamHI site was introduced into a part of the 3' side, was synthesized.

Using mRNAs obtained from a mouse T cell line, RLM-11 (Cell, _, 1109 (1992)), as a template, and F1 and R1 as PCR primers, RT-PCR was carried out using a thermal sequencer (GeneAmp PCR System 9600, Perkin Elmer) under conditions of 180 seconds ×1 at 95° C. →60 seconds at 95° C., 60 seconds at 55° C., 60 seconds at 72° C.)× 15→180 seconds at 72° C. As a result, a fragment of about 520 bp (hereinafter referred to as "MFas") was obtained and inserted into the multi-cloning site, HindIII-BamHI restriction enzyme site, of pBluescript (trade name, Promega), hereinafter referred to as "pBSMFas".

EXAMPLE 2

Preparation of PCR Product of Human PPAR α, γ or γ receptor

The following primers were prepared based on the structure of human PPAR α, γ or γ receptor described by R. Mukherjee et al., (see *J. Steroid Biochem. Molec. Biol.*, 51, 157 (1994)); M. E. Greene et at. (see *Gene Expression*, 4, 281 (1995)); A. Elbrecht et al. (see *Biochem. Biophys. Res. Commun.*, 22, 431 (1996)); or Schmidt (see *Mol. Endocrinol.*, 6, 1134 (1992).

F2: A sense primer, 5'-AACCAGCACCATCTGGTCGCGATGGT-3' (SEQ ID NO:3), corresponding to the 5' non-translation region and N-terminal amino acids $Met^1$- $Val^2$ of the human PPAR ax, was synthesized.

R2: An antisense primer, 5'-AGGTGTGGCTGATCTGAAGGAACTC A-3' (SEQ ID NO:4), corresponding to the 3' non-translation region of the human PPAR α and a amino acid termination codon, was synthesized.

F3: A sense primer, 5'-AGAAATGACCATGGTTGACACAGAGA-3' (SEQ ID NO:5), corresponding to the 5' non-translation region and N-terminal amino acids $Met^1$–$Met^8$ of the human PPAR γ (γ1 subtype), was synthesized.

R3: An antisense primer, 5'-AAATGTTGGCAGTGGCTCAGGACTC T-3' (SEQ ID NO:6), corresponding to the 3' non-translation region of the human PPAR γ (γ1 subtype), was synthesized.

F4: A sense primer, 5'-AGATCAGCCATGGAGCAGCCACAGGA-3' (SEQ ID NO:7), corresponding to the 5' non-translation region and N-terminal amino acids $Met^1$ -$Glu^6$ of the human PPAR γ, was synthesized.

R4: An antisense primer, 5'-ATTGGAGTCTGCAGGGAGGCCTGGG T-3' (SEQ ID NO:8), corresponding to the 3' non-translation region of the human PPAR 6, was synthesized.

Using Superscript Human Liver cDNA Library (trade name, Cat. No. 10422-012, manufactured by GIBCO BRL) as cDNA library, and F2 and R2, F3 and R3 or F4 and R4 as PCR primers, PCR was carried out using a thermal sequencer (GeneAmp PCR System 9600, manufactured by Perkin Elmer) under conditions of 120 seconds ×1 at 95° C. →(60 seconds at 95° C., 90 seconds at 60° C., 120 seconds at 72° C.)×30 →180 seconds at 72° C. As a result, the human PPAR (x of 1450 bp, the human PPAR y of 1469 bp and the human PPAR γ of 1367 bp were obtained, and they were inserted into a T-vector (pT7Blue-T vector, Cat. No. 69836-1) manufactured by Novagen to confirm their complete nucleotide sequences.

EXAMPLE 3

Effector Protein Expression System; Construction of Expression Vector Comprising cDNA Encoding Fusion Protein (Gal4 chimeric receptor protein) of Gal4 Protein and Nuclear Receptor Ligand Binding Region A vector capable of expressing Gal4 chimeric receptor protein as a structural gene under control of SV40 promoter was constructed using Pica Gene Basic Vector 2 (trade name, PGBV2, Cat. No. 309-04821, manufactured by Toyo Ink) as a basic vector. That is, this was completed by excising a luciferase structural gene of PGBV2 using restriction enzymes NcoI and XbaI and inserting Gal4 chimeric receptor protein-encoding cDNA prepared in the following manner.

(1) Insertion of DNA encoding DNA binding region of Gal4 transcription factor into expression vector.

As cDNA of the DNA binding region of a yeast basal transcription factor Gal4 protein, a DNA encoding an amino acid sequence of the 1st to 147th positions of Gal4 was amplified by PCR under the same conditions of Example 2 using pGBT9 (manufactured by Clontech, Cat. No. K1605-A) as the template. The following F5 and R5 were used as primers.

F5: A sense primer, 5'-GCAAGCTTCACCATGAAGCTACTGTCTTC TATCGAAC3' (SEQ ID NO:9), corresponding to an N-terminal side amino acid sequence of the 1st to 8th positions of the DNA binding region of Gal4, in which a HindIII site and, in order to obtain effective protein expression in mammal cells, a kozak sequence were added to a part of the 5' side, was synthesized.

R5: An antisense primer, 5'-AGCCATGGCCGGCGATACAGTCAACT GTCTTTC-3' (SEQ ID NO:10), corresponding to a C-terminal side amino acid sequence of the 141st to 147th positions of the DNA binding region of Gal4, in which an NcoI site was added to a part of the 5' side, was synthesized, and the thus synthesized primer was amplified by PCR under the same conditions of Example 2. As a result, an amplified DNA of about 465 bp, after confirmation of its complete nucleotide sequence, was recombined with the HindIII/NcoI site in the PGBV2 vector (hereinafter referred to as "pGVgal").

(2) Preparation of DNA encoding human PPAR γ ligand binding region and construction of Gal4-human PPAR γ chimeric receptor protein expression vector Using the complete human PPAR γ-encoding cDNA isolated from a human liver cDNA library in accordance with the procedure of Example 2 as a template and synthesizing the following primers, a DNA encoding a sequence of $Ser^{178}$ to $Tyr^{178}$ including the human PPAR γ ligand binding region was amplified by PCR under the same conditions of Example 1.

F6: A sense primer, 5'-GCCATGGCTCCTAAGAAGAA-GCGTAAGGTAGGATCCCATAATGCCATCAGGTTT-GGGCGGAT-3' (SEQ ID NO:11), corresponding to a sequence of $Ser^{176}$ to $Met^{185}$, in which an NcoI site, an SV40 T antigen-originated nuclear transport signal (Ala Pro Lys Lys Lys Arg Lys Val Gly) (SEQ ID NO:24) and a BamHI site were arranged in this order on the 5' side, was synthesized.

R6: An antisense primer, 5'-CCTCTAGACTAGCTGGCATAGTCGGGCACGTCGT AGGGGTAGTCGACGTACAAGTCCTTGTAGATCTCC-3' (SEQ ID NO: 12), corresponding to a sequence of $Glu^{472}$ to Tyr$^{478}$, in which an SalI site, an influenza hemagglutinin epitope (Tyr Pro Tyr Asp Val Pro Asp Tyr Ala) (SEQ ID NO:20) as an epitope tag sequence for use in the detection of expressed protein, a translation termination codon and an XbaI site were arranged in this order, was synthesized.

The luciferase structural gene in the above pGVgal was excised out both from the XbaI site of the region downstream of luciferase structural gene and the NcoI site at the region downstream of the DNA encoding the Gal4 DNA binding region, and replaced by a DNA encoding the human PPAR γ ligand binding region, thereby obtaining the effector protein expression vector of interest (hereinafter referred to as "pGVgal/γLBD").

(3) Preparation of DNA encoding human PPAR α ligand binding region and construction of Gal4-human PPAR α chimeric receptor protein expression vector A PPAR α ligand binding region structural gene was synthesized by synthesizing the following primers comprising the human PPAR α ligand binding region and carrying out PCR amplification under the same conditions of Example 2. The thus obtained PPAR α ligand binding region structural gene was inserted into the BamHI-SelI restriction enzyme site of the pGVgal/γLBD vector synthesized above which had been digested with these restriction enzymes to selectively excise the PPAR γ ligand binding region structural gene to construct a Gal4-human PPAR a chimeric receptor protein expression vector (hereinafter referred to as "pGVgal/αLBD").

F7: A sense primer, 5'-CACGGATCCCACAACGCGATTCGTTTTGG ACGA-3' (SEQ ID NO:13), corresponding to an amino acid sequence of Ser$^{167}$ to Arg$^{175}$ of the human PPAR a and having a BamHI site in its 5' side, was synthesized.

R7: An antisense primer, 5'-ATGGTCGACGTACATGTCCCTGTAGA T C T C C T G-3' (SEQ ID NO:14), corresponding to an amino acid sequence of Gln$^{461}$ to Tyr$^{468}$ of the human PPAR cc and having an Sail site in its 5' side, was synthesized.

(4) Preparation of DNA encoding human PPAR 8 ligand binding region and construction of Gal4-human PPAR 3 chimeric receptor protein expression vector A PPAR γ ligand binding region structural gene was synthesized by synthesizing the following primers comprising the human PPAR γ ligand binding region and carrying out PCR amplification under the same conditions of Example 2. The thus obtained PPAR 8 ligand binding region structural gene was inserted into the BamHI-SalI restriction enzyme site of the pGVgal/γLBD vector synthesized above which had been digested with these restriction enzymes to selectively excise the PPAR γ ligand binding region structural gene to construct the Gal4-human PPAR γ chimeric receptor protein expression vector (hereinafter referred to as "pGVgal/LBD").

F8: A sense primer, 5'-CACGGATCCCACAACGCTATCCGTTTTGG TCGG-3' (SEQ ID NO:15), corresponding to an amino acid sequence of Ser$^{139}$ to Arg$^{147}$ of the human PPAR γ and having a BamHI site in its 5' side, was synthesized.

R8: An antisense primer, 5'-ATGGTCGACGTACATGTCCTTGTAGA T C T C CT G3' (SEQ ID NO:16), corresponding to an amino acid sequence of Gln$^{434}$ to Tyi$^{441}$ of the human PPAR 5 and having an Sail site in its 5' side, was synthesized.

EXAMPLE 4

Reporter gene; Construction of reporter plasmid in which TK promoter and MFas structural gene are arranged in region downstream of Gal4 transcription factor responsive element An expression vector pTKβ (manufactured by Clontech, Cat. No. 6179-1) under control of herpes simplex virus thymidine kinase (TK) promoter was used. NotI sites upstream and downstream of the β-galactosidase structural gene of pTKβ were digested, and both termini are smooth-ended. Next, a DNA encoding the MFas protein, as a DNA to be inserted, was excised from pBSMFas by using restriction enzymes HindIII and BamHI and blunt-ended. Both of the DNAs were ligated to select a clone in which the MFas structural gene was connected to the region downstream of TK promoter in the forward direction. The thus obtained plasmid pTK-MFas of about 4400 bp contains a DNA encoding MFas protein under control of the TK promoter. Next SalI site located in the region upstream of the TK promoter of plasmid pTK-MFas was digested and blunt-ended, and then a multi-cloning site was inserted as a linker DNA (SEQ ID NO:17, EcoRI-SalI-KpnI-EcORV-SacI-NotI):

5'-GAATTCGTCGACGGTACCGATATCGAGCTCGCG-GCCGC-3'

3'-CTTAAGCAGCTGCCATGGCTATAGCTCGAGCG-CCGGCG-5' (SEQ ID NO:21)

To obtain pTK-MFas-ML1(5'-EcoRI-SalI-KpnI-EcORV-SacI-NotI-3').

An enhancer region was produced by inserting a Gal4 responsive element, 5'-T (CGACGGAGTACTGTCCTCCG)×4 AGCT-3' (SEQ ID NO:18), having 4 repetition of a basal unit (UAS) and SalI site/Sac site on both ends, into the Sail-SacI site inside the pTK-MFas-ML1 multi-cloning site. As a result, p4xUAS-TK-MFas (about 4600 bp) in which the 4×UAS, TK promoter and MFas structural gene were arranged in this order was constructed.

Each of the thus obtained expression vector pSVgal/αLBD, pSVgal/γLBD and pSVgal/δLBD, the reporter plasmid and pSV2bsr (manufactured by Kaken Pharmaceutical, Cat. No. KK-500) were subjected to linearization by the treatment with a restriction enzyme AatiI or NotI or not treated (circular form), respectively, and introduced at a quantitative ratio of 1:1:0.1 into mouse fibroblast L929 using Lipofect AMINE (manufactured by GIBCO; Cat. No. 4=18324-012). Stably transformed cells were selected in accordance with the method (blasticidin S selection) described in *Exp. Cell Res.*, 197, 229 (1991).

EXAMPLE 5

Selection of Ligand Responsive Clone

After 1 to 2 weeks of selection, observed colonies were subjected to cell cloning by limiting dilution and grown. For example, each subclone was suspended in Eagle's MEM containing 10% fetal calf serum (FCS) in a density of 2×10$^4$ cells/100 µl, dispensed into wells of 96 well microtiter plate and cultured at 370C for 4 to 6 hours in an atmosphere of 5% carbon dioxide. Cells which die significantly in the presence of a ligand were selected using CS-045 and BRL-49653 known as PPAR γ ligands (see *Cell*, 83, 863 (1995), *Endocrinology*, 137, 4189 (1996) and *J. Med. Chem.*, 39, 665 (1996)), carbacyclin and ETYA known as PPAR α ligands (cf. *J. Steroid Biochem. Molec. Biol.*, 51, 157 (1994), *Cell Structure and Function*, 18, 267 (1993), *Gene & Development*, 10, 974 (1996) and *Eur. J. Biochem.*, 233, 242 (1996)), carbacyclin known as PPAR γ ligand (see *Gene & Development*, 10, 974 (1996)) and a compound disclosed by Merck (see the compound of Example 7 in PCT International Application International Publication No. 9728149).

That is, each sample of these compounds having two times higher concentration than their final concentration 10 µM was added to each of the above culture wells, and the cells were again cultured for 40 hours. After discarding the supernatant, the resulting plate was soaked in a Crystal Violet solution (0.75% Crystal Violet-0.25% NaCl-1.75% formaldehyde in 50% ethanol) at room temperature for 20 minutes and then washed twice with phosphate buffered saline (PBS), thereby effecting staining of survived cells (see Cell, 66, 233 (1991)). Absorbance of each well of the plate was directly measured at 570 nm using a microplate reader.

EXAMPLE 6

Cell Death Assay Using L929 Cells Stably Introduced with Plasmid Encoding PPAR γ, α or γ ligand Each of the clones obtained in Example 5 having the highest responsive ability was cultured by the above method, cell death of the thus cultured cells was induced by the above compounds by the above method and then the survived cells were stained to measure the absorbance. The cell death appeared significantly after 24 hours and was completed during 36 to 40 hours by reaching to the plateau stage.

Dose-dependent changes in the number of intact cells after 40 hours of treatment of the PPAR y ligand-responsive clone with CS-045 and BRL-49653 are shown in FIG. 1(A), and dose-dependent changes in the number of intact cells after treatment of control cells (L929) with these compounds in the same manner are shown in FIG. 1(B). Dose-dependent changes in the number of intact cells after 40 hours of treatment of the PPAR y ligand-responsive clone with carbacyclin and Wy-14643 are shown in FIG. 2(A), and dose-dependent changes in the number of intact cells after treatment of control cells (L929) with these compounds in the same manner are shown in FIG. 2(B).

Also, dose-dependent changes in the number of intact cells after 40 hours of treatment of the PPAR ax ligand-responsive clone with carbacyclin, ETYA, Wy-14634 and CS-045 are shown in FIG. 3(A), and dose-dependent changes in the number of intact cells after treatment of control cells (L929) with these compounds in the same manner are shown in FIG. 3(B).

Also, dose-dependent changes in the number of intact cells after 40 hours of treatment of the PPAR α ligand-responsive clone with carbacyclin, the compound of Merck, ETYA and CSO045 are shown in FIG. 4(A), and dose-dependent changes in the number of intact cells after treatment of control cells (L929) with these compounds in the same manner are shown in FIG. 4(B).

Also, the ratio of the number of intact cells when each compound was replaced by a solvent was expressed as 100% in each drawing.

As apparent from FIG. 1, in the case of the cells into which the expression vector of effector protein Gal4-human PPAR y chimeric receptor protein was stably introduced, CS-045 and BRL49653 known as PPAR γ agonists did not show direct toxicity upon normal L920 cells, but caused significant death of responsive cells in a dose-dependent manner. In addition, although they are the same PPAR γ agonist, the compound having higher binding affinity for PPAR γ protein or larger transcription activation ability (cf. Biochem. Biophys. Res. Commun., 224, 431 (1996)) showed remarkable cell killing action at a lower concentration.

Figure 2:
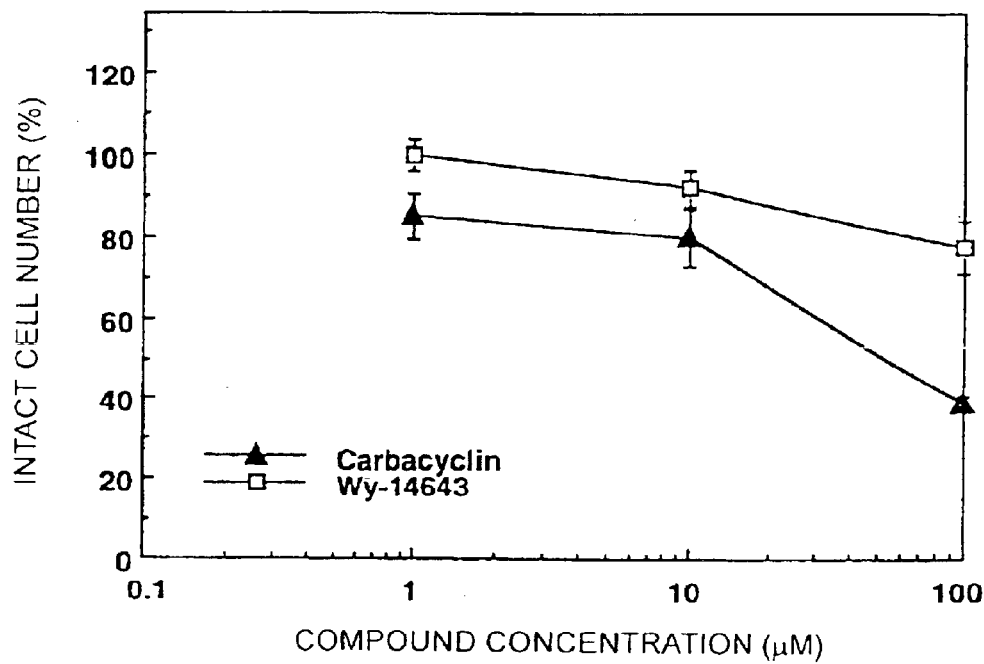
FIG. 2 is a graph showing dose-dependent changes in the number of intact cells after treatment of each compound by carrying out a cell death assay using PPAR γ ligand-responsive L929 cells. In the drawing, (A) shows a case of PPAR γ ligand-responsive cells, and (B) shows a case of normal L929 cells.
Figure 2:
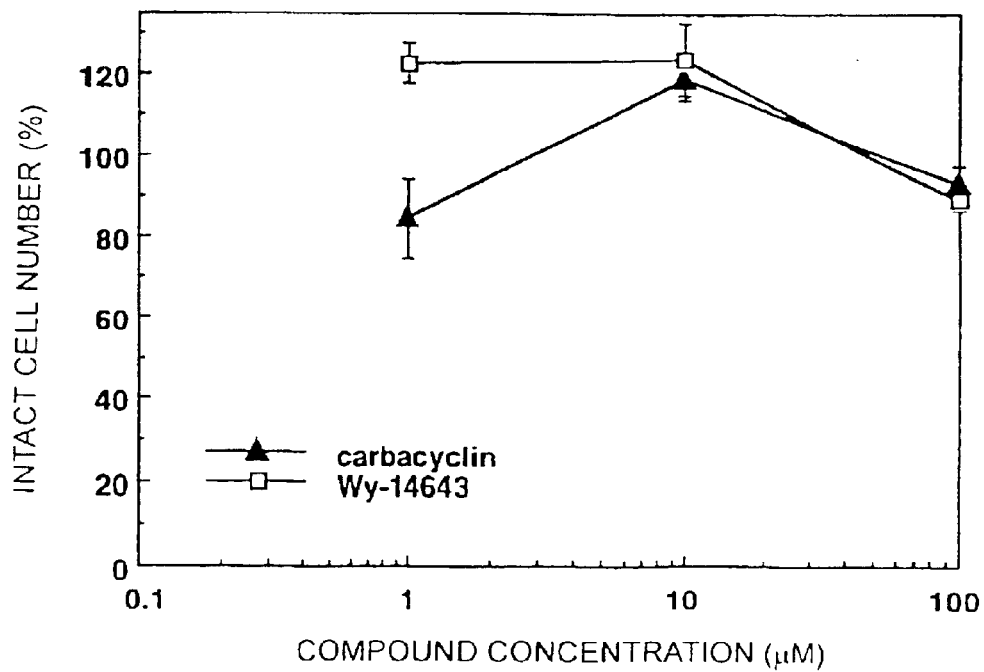

As apparent from FIG. 2, carbacyclin and Wy-14643 known as a PPAR α agonists do not cause cell death at respective concentrations of 10 µM or less and 100 µM or less which do not exert toxicity upon the cells. Particularly, at a concentration of 10 µM or less by which carbacyclin does not show PPAR γ agonist activity (cf. Genes & Development, 10, 974 (1996)), it does not cause cell death in the PPAR γ ligand responsive cells.

Figure 3:
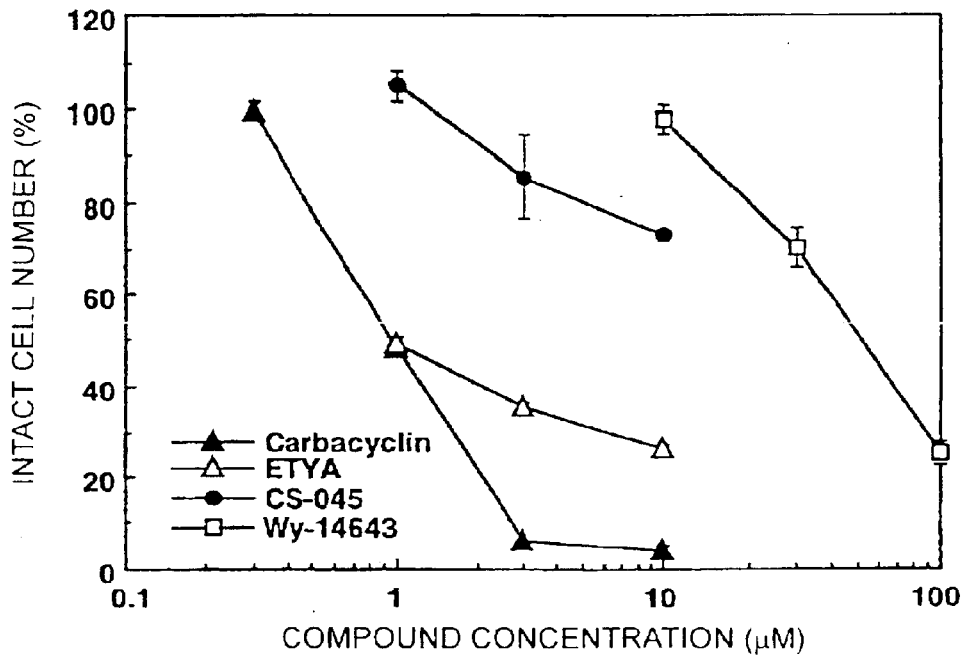
FIG. 3 is a graph showing dose-dependent changes in the number of intact cells after treatment of each compound by carrying out a cell death assay using PPAR α ligand-responsive L929 cells. In the drawing, (A) shows a case of PPAR a ligand-responsive cells, and (B) shows a case of normal L929 cells.
Figure 3:
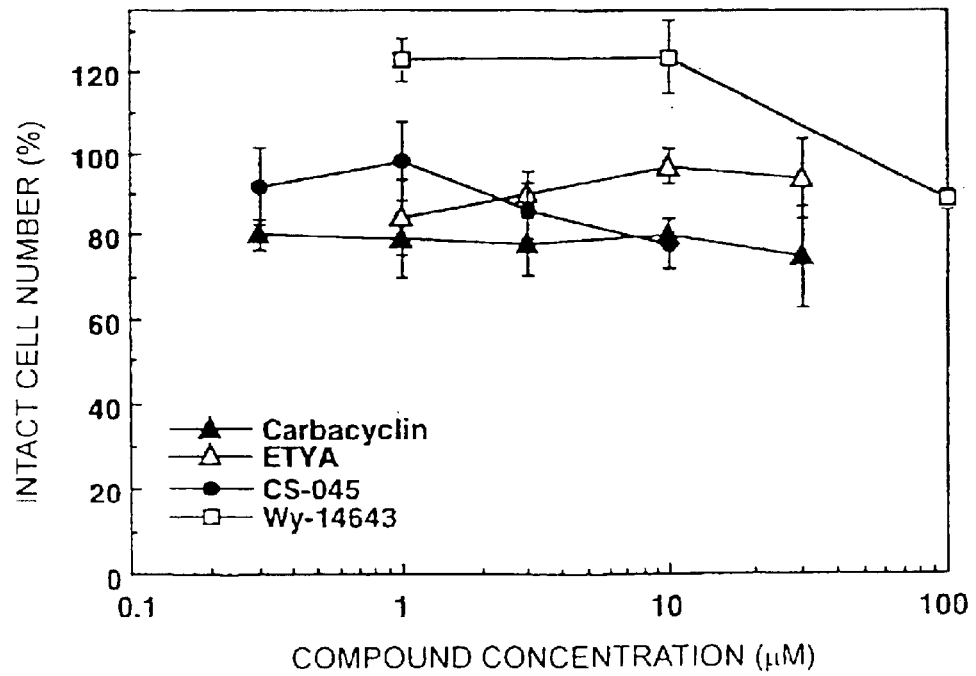

As apparent from FIG. 3, carbacyclin, ETYA and Wy-14643 known as PPAR a agonists cause dose-dependent cell death. On the other hand, CS-045 known as a PPAR γ agonist does not cause cell death at a concentration of 10 µM or less which does not show toxicity. In addition, although the former three are the same PPAR α agonist, a compound having higher binding affinity for PPAR a protein or larger transcription activation ability showed remarkable cell killing action at a lower concentration.

Figure 4:
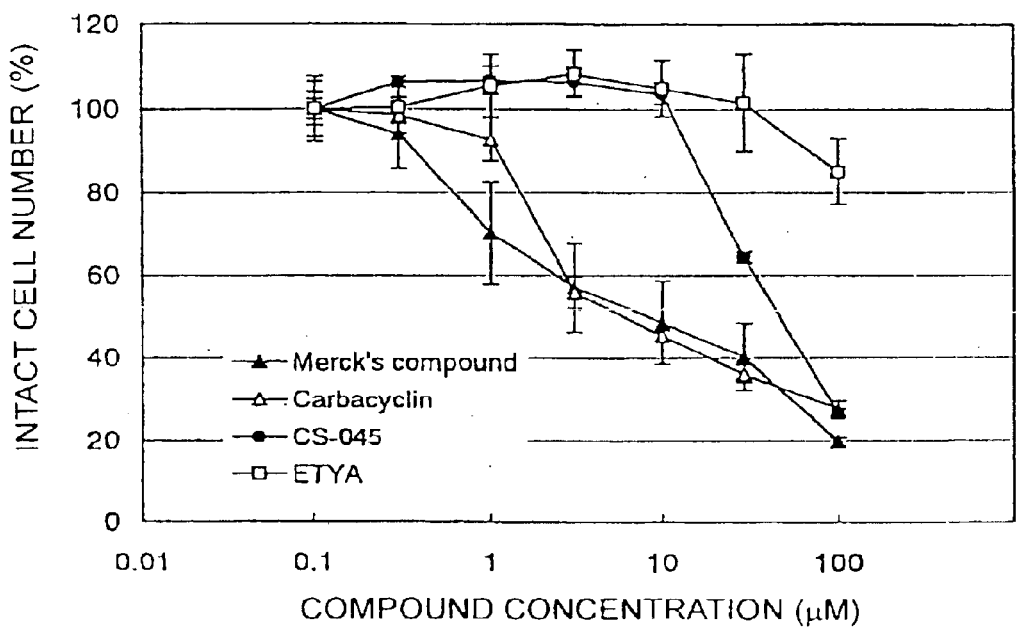
FIG. 4 is a graph showing dose-dependent changes in the number of intact cells after treatment of each compound by carrying out a cell death assay using PPAR δ ligand-responsive L929 cells. In the drawing, (A) shows a case of PPAR δ ligand-responsive cells, and (B) shows a case of normal L929 cells.
Figure 4:
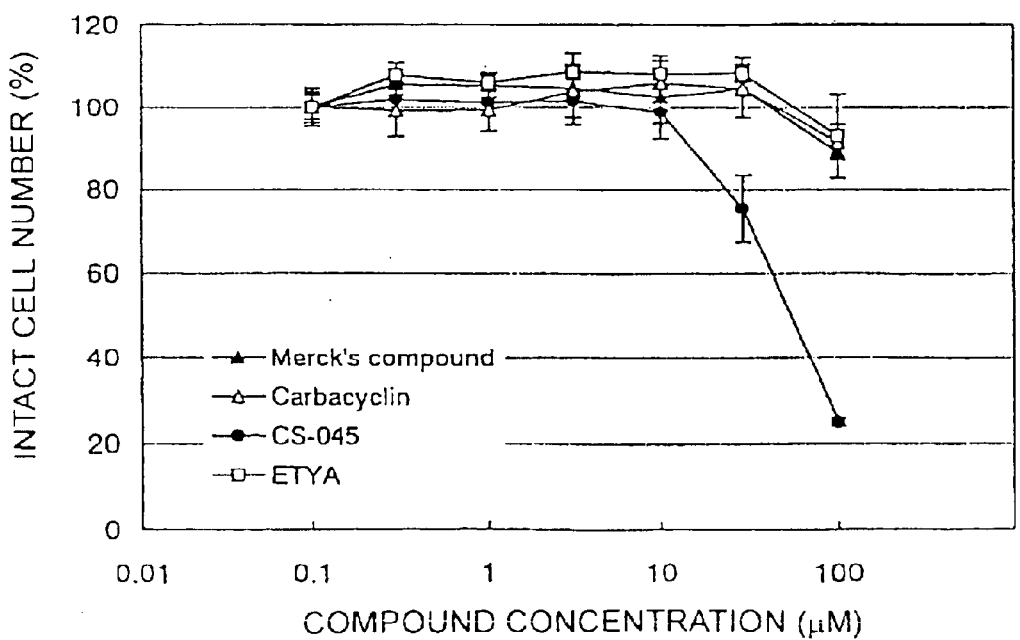

As apparent from FIG. 4, carbacyclin and Merck's compound known as PPAR δ agonists cause dose-dependent cell death. On the other hand, CSO045 known as a PPAR γ agonist and ETYA known as a PPAR a agonist do not cause cell death at a concentration of 10 µM or less which does not show toxicity. In addition, though the former two compounds are the same PPAR γ agonist, the compound having higher binding affinity for PPAR δ protein or larger transcription activation ability showed remarkable cell killing action at a lower concentration.

Based on the results shown in FIGS. 1, 2, 3 and 4, it was revealed that, when cell death is mediated by the over-expression of a functional MFas peptide, cell death of PPAR γ ligand-responsive cells occurs in good correlation with the action strength of the PPAR γ ligand, that of PPAR ca ligand-responsive cells correlatively with the action strength of the PPAR a ligand, and that of PPAR γ ligand-responsive cells with the PPAR 5 ligand. In addition, the cell death occurred when not only the PPAR but also other nuclear receptors were used and when the PPAR of not only human but also other animal origin was used. When the reporter assay of the invention is used, nuclear receptor ligands can be evaluated easily and specifically by obtaining highly ligand-responsive clones prepared by stably introducing respective plasmid therein. Additionally, since the amount of compounds to be tested effective for their evaluation by the reporter assay markedly coincides with the range of concentrations showing the cell-killing action in the system of the invention, this is an excellent method by which potency of respective ligands can be evaluated simultaneously.

What is claimed is:

1. A composition comprising: (a) a plasmid DNA comprising in 5' to 3' direction, a GAL4 responsive element a promoter, and a polynucleotide encoding a transmembrane region and an apoptosis-inducing domain of a Fas antigen; and (b) a plasmid DNA encoding a fusion protein comprising in a 5' to 3' direction a GAL4 DNA binding region and a nuclear receptor ligand binding region selected from the group consisting of: amino acids 166 to 478 of human PPARγ1 subtype receptor, amino acids 194 to 506 of human PPARγ2 subtype receptor, amino acids 164 to 475 of mouse PPARγ1 subtype receptor, amino acids 194 to 505 of mouse PPARγ2 subtype receptor, amino acids 157 to 468 of human PPARα receptor, amino acids 157 to 468 of rat PPARα receptor, amino acids 129 to 441 of human PPARδ receptor, and amino acids 128 to 440 of mouse PPARδ receptor.

2. The composition according to claim 1, wherein said polynucleotide encodes a transmembrane region and an apoptosis-inducing domain of a Fas antigen represented by amino acids 136 to 305 of mouse Fas antigen (SEQ ID NO:23) or amino acids 145 to 319 of human Fas antigen (SEQ ID NO:22).

3. The composition according to claim 1, wherein said polynucleotide further encodes a signal peptide region of a Fas antigen in frame with the transmembrane region and an apoptosis-including domain of Fas antigen, and wherein the transmembrane region and the apoptosis-including domain of a Fas antigen are represented by amino acids 136 to 305 of mouse Fas antigen (SEQ ID NO:23) or amino acids 145 to 319 of human Fas antigen (SEQ ID NO:22).

4. The composition according to claim 3, wherein said polynucleotide encodes a Fas antigen signal peptide region represented by amino acids −21 to 14 of mouse Fas antigen (SEQ ID NO:23) or amino acids −16 to 23 of human Fas antigen (SEQ ID NO:22).

* * * * *